(12) United States Patent
Jach et al.

(10) Patent No.: US 10,345,249 B1
(45) Date of Patent: Jul. 9, 2019

(54) SYSTEM FOR DETECTING AND REAL TIME PROCESSING X-RAY PULSES FROM MICROCALORIMETER DETECTORS

(71) Applicant: The United States of America, as represented by the Secretary of Commerce, Washington, DC (US)

(72) Inventors: Terrence J. Jach, Washington, DC (US); Stephen M. Thurgate, Kardinya (AU)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 0 days.

(21) Appl. No.: 15/843,319

(22) Filed: Dec. 15, 2017

(51) Int. Cl.
*G01N 23/20033* (2018.01)
*G01K 7/00* (2006.01)
*H01J 37/244* (2006.01)
*G01N 23/083* (2018.01)

(52) U.S. Cl.
CPC ....... *G01N 23/20033* (2013.01); *G01K 7/006* (2013.01); *G01N 23/083* (2013.01); *H01J 37/244* (2013.01)

(58) Field of Classification Search
CPC ........... G01N 23/20033; G01N 23/083; G01K 7/006; H01J 37/244
USPC ...................................................... 250/252.1
See application file for complete search history.

(56) References Cited

U.S. PATENT DOCUMENTS

| | | | |
|---|---|---|---|
| 5,634,718 | A | 6/1997 | Martinis et al. |
| 5,684,850 | A | 11/1997 | Warburton et al. |
| 5,873,054 | A | 2/1999 | Warburton et al. |
| 5,880,468 | A | 3/1999 | Irwin et al. |
| 6,239,431 | B1 | 5/2001 | Hilton et al. |
| 6,455,849 | B1 | 9/2002 | Hilton et al. |
| 6,609,075 | B1 | 8/2003 | Warburton et al. |
| 7,521,682 | B1 | 4/2009 | Holland et al. |

(Continued)

OTHER PUBLICATIONS

K. D. Irwin, et al., X-ray detection using a superconducting transition-edge sensor microcalorimeter with electrothermal feedback, Appl. Phys. Lett, 1996, p. 1945, 69.

(Continued)

*Primary Examiner* — David P Porta
*Assistant Examiner* — Meenakshi S Sahu
(74) *Attorney, Agent, or Firm* — Office of Chief Counsel for National Institute of Standards and Technology

(57) ABSTRACT

An x-ray spectrometer system includes: an excitation source that produces excitation particles and irradiates a sample with the excitation particles such that the sample produces x-rays; thermal detectors that: detect the x-rays from the sample; and produce digital x-ray data in response to detecting the x-rays from the sample, the x-ray data including x-ray pulses; and an analyzer that includes a multichannel receiver that receives, in parallel, the digital x-ray data from the thermal detectors and that: rejects pulse pileup in the digital x-ray data and produces pass data from the digital x-ray data; subjects the pass data to an optimal filter to produce filter data; determines a pulse height of x-ray pulses in the filter data to produce pulse data; combines the pulse data to produce combined data; and calibrates the combined data to produce calibrated data.

3 Claims, 12 Drawing Sheets

(56) References Cited

U.S. PATENT DOCUMENTS

2011/0064191 A1* 3/2011 Toth ............... G01N 23/20033
378/53

OTHER PUBLICATIONS

Wollman, D.A., et al., High-resolution, energy-dispersive microcalorimeter spectrometer for x-ray microanalysis, Journal of Microscopy, 1997, 196-223, 188.

D. A. Wollman, et al., High Resolution Microcalorimeter Energy Dispersive Spectrometer for X-ray Microanalysis and Particle Analysis, Characterization and Metrology for ULSI Technology, AIP pub. 1998, 799-807.

Belli, F., et al., Application of a digital pileup resolving method to high count rate neutron measurements, Review of Scientific Instruments, 2008, 79.

Bolic, M., et al., Pileup correction algorithms for very high count rate gamma-ray spectrometry with NaI(T1) detectors, IEEE Transactions on Instrumentation and Measurement, 2010, 122-130, 59(1).

Dragone, A., et al., The PDD ASIC: Highly efficient energy and timing extraction for high-rate applications, IEEE Nuclear Symposium Conference Record, 2005, 914-918.

Frizzi, T., et al., The SIDDHARTA chip: a CMOS multi-channel circuit for silicon drift detectors readout in exotic atoms research, IEEE Nuclear Science Symposium Conference Record, 2006, 850-856.

Germano, G., et al., An investigation of methods of pileup rejection for 2-D array detectors employed in high resolution PET, IEEE Transactions on Medical Imaging, 1991, 223-227, 10(2).

Grinyer, G.F., et al., Pile-up corrections for hight-precision superallowed $\beta$ decay half-life measurements via Y-ray photopeak counting, Nuclear Instruments and Methods in Physics Research, 2007, 1005-1033, 579.

Guo, W, et al., The Monte Carlo approach MCPUT for correcting pile-up distorted pulse-height spectra, Nuclear Instruments and Methods in Physics Research, 2004, 520-529, 531.

Jordanov, V.I., et al., Digital pulse-shape analyzer based on fast sampling of an integrated charge pulse, 1995, 683-687, 42(4).

Popov, S., et al., Camac standard high-speed precise spectrometer, IEEE, 1995, 375-378.

Raad, M.W., et al., Novel peak detection algorithms for pileup minimization in gamma ray spectroscopy, Instrumentation and Measurement Technology Conference, IEEE, 2006, 2240-2243.

Bandler, S., et al., NTD-GE-based microcalorimeter performance, Nuclear Instruments and Methods in Physics Research A, 2000, 273-277.

Li, Q., et al., Spectral analysis of nanomaterials using a transition-edge sensor microcalorimeter mounted on a field-emission scanning electron microscope, Japanese Journal of Applied Physics, 2008, 4835-4838, 47(6).

Redfern, D., et al., Microcalorimeter for industrial applications, Journal of Research of the National Institute of Standards and Technology, 2002, 621-626, 107(6).

Sakamoto, T., et al., Development of an ion and electron dual focused beam apparatus for three-dimensional microanalysis, Japanese Journal of Applied Physics, 1998, 2051-2056, 37.

* cited by examiner

SYSTEM FOR DETECTING AND REAL TIME PROCESSING X-RAY PULSES FROM MICROCALORIMETER DETECTORS

STATEMENT REGARDING FEDERALLY SPONSORED RESEARCH

This invention was made with United States Government support from the National Institute of Standards and Technology (NIST), an agency of the United States Department of Commerce. The Government has certain rights in the invention. Licensing inquiries may be directed to the Technology Partnerships Office, NIST, Gaithersburg, Md., 20899; voice (301) 301-975-2573; email tpo@nist.gov; reference NIST Ser. No. 15/843,319.

BRIEF DESCRIPTION

Disclosed is a process for performing real time analysis of x-ray pulses from a plurality of thermal detectors, the process comprising: introducing a sample to an x-ray spectrometer comprising the thermal detectors, the thermal detectors comprising a micro-calorimeter absorber and a temperature sensor; irradiating the sample with excitation particles; producing x-rays by the sample in response to irradiation with the excitation particles; detecting the x-rays by the thermal detectors; producing digital x-ray data by the thermal detectors in response to detecting the x-rays from the sample; receiving, in parallel by a multichannel receiver, the digital x-ray data from the thermal detectors, the x-ray data comprising a plurality of x-ray pulses; rejecting pulse pileup in the digital x-ray data to produce pass data from the digital x-ray data; subjecting the pass data to a digital filter to produce filter data; determining a pulse height of x-ray pulses in the filter data to produce pulse data; combining the pulse data to produce combined data; and calibrating the combined data to produce calibrated data to perform analysis, in real time, of the x-ray pulses from the thermal detectors.

Also disclosed is a process for performing real time analysis of x-ray pulses from a plurality of thermal detectors, the process comprising: receiving digital x-ray data from the thermal detectors comprising a micro-calorimeter absorber and a temperature sensor, the x-ray data comprising a plurality of x-ray pulses; rejecting pulse pileup in the digital x-ray data to produce pass data from the digital x-ray data; subjecting the pass data to a digital filter to produce filter data; determining a pulse height of x-ray pulses in the filter data to produce pulse data; combining the pulse data to produce combined data; and calibrating the combined data to produce calibrated data to perform analysis, in real time, of the x-ray pulses from the thermal detectors.

Further disclosed is an x-ray spectrometer system comprising: an excitation source that produces excitation particles and irradiates a sample with the excitation particles such that the sample produces x-rays in response to irradiation with the excitation particles; a plurality of thermal detectors, the thermal detectors comprising a micro-calorimeter absorber and a temperature sensor, and that: detects the x-rays from the sample; and produces digital x-ray data in response to detecting the x-rays from the sample, the x-ray data comprising a plurality of x-ray pulses; and an analyzer that comprises a multichannel receiver that receives, in parallel, the digital x-ray data from the thermal detectors and that: rejects pulse pileup in the digital x-ray data and produces pass data from the digital x-ray data; subjects the pass data to a digital filter to produce filter data; determines a pulse height of x-ray pulses in the filter data to produce pulse data; combines the pulse data to produce combined data; and calibrates the combined data to produce calibrated data in which analysis is performed, in real time, on the x-ray pulses from the thermal detectors.

BRIEF DESCRIPTION OF THE DRAWINGS

The following descriptions should not be considered limiting in any way. With reference to the accompanying drawings, like elements are numbered alike.

DETAILED DESCRIPTION

Figure 1:
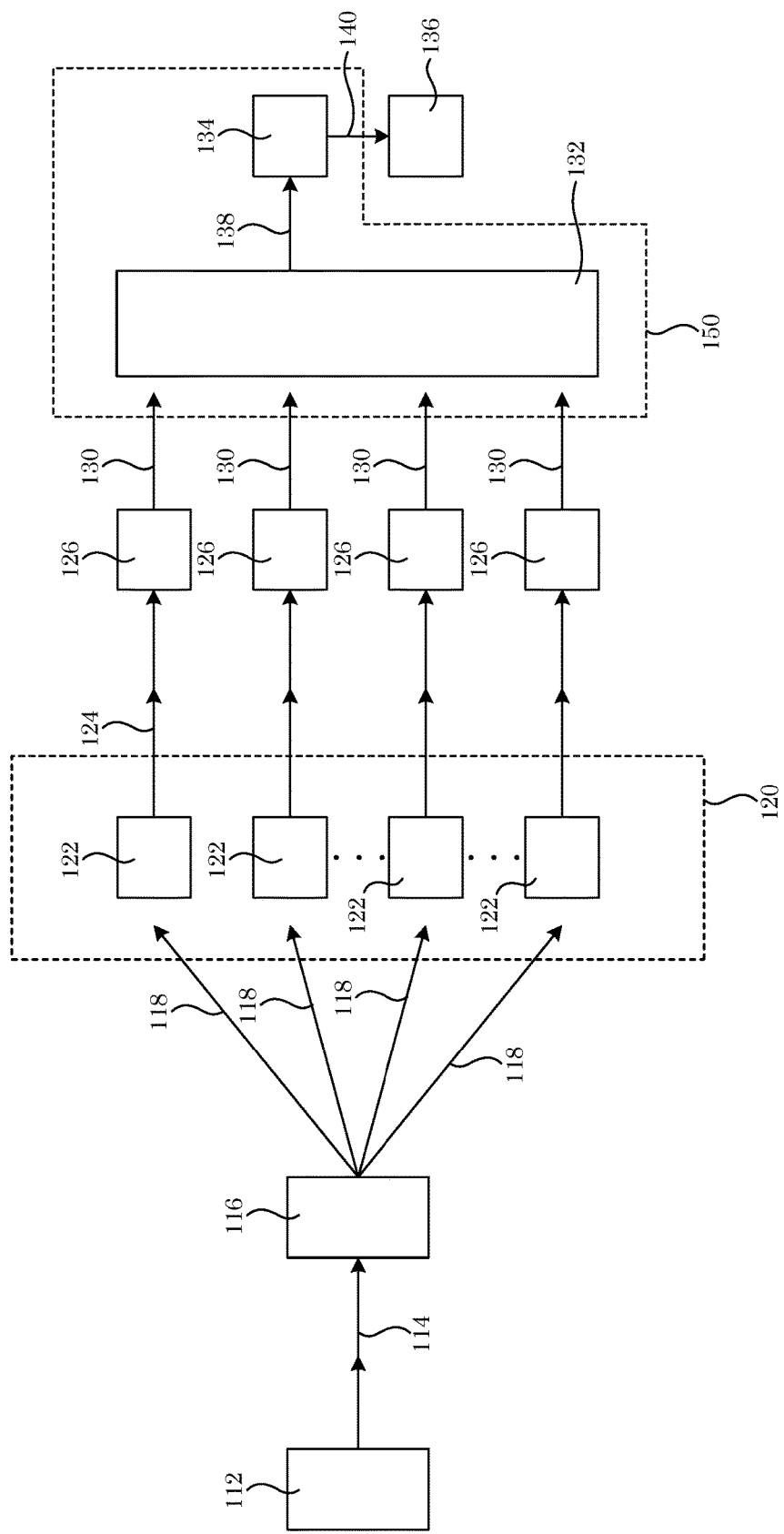
FIG. 1 shows an x-ray spectrometer system.

A detailed description of one or more embodiments is presented herein by way of exemplification and not limitation.

Advantageously and unexpectedly, it has been discovered that an x-ray spectrometer system herein provides pulses from thermal detectors that include temperature sensors to be converted into a histogram of x-ray energies in real time. The x-ray spectrometer system identifies and rejects pileup and corrupted pulses to an arbitrary degree, filters the pulses for noise in an optimal manner, and determines pulse heights. Pulses from multiple absorbers are corrected for individual characteristics and combined to provide a single histogram of counts versus x-ray energy. Moreover, the x-ray spectrometer system provides x-ray detection and determination of x-ray energies over a wide range with high resolution.

X-ray detectors can be classified as energy dispersive and produce pulses of charged particles that can be collected. A pulse amplitude is proportional to an energy of an absorbed x-ray photon. Some x-ray detectors produce pulses from 1-10 microseconds. Pulses can be measured against a background in which noise or perturbations are absent so that the background is free of a previous pulse, or prior pulses can be characterized and compensated. Pulses can be shaped optimally, and system noise can be filtered from signals.

Conventional energy-dispersive x-ray detectors have pulse shapes and time constants to which frequency-dependent filtration was used to minimize noise and to shape the pulse for determination of the pulse height. Some energy-dispersive detectors provide an output pulse that can be calibrated in terms of a physical detection process. A histogram of the pulse heights forms a spectrum that is stable when a calibration has been performed. In conventional detectors in a presence of certain correlations, e.g., the Fano Effect, resolution can be based on creation of charges with limitation to 120 electron volts (eV) for x-rays from 1 keV to 10 keV energy.

The x-ray spectrometer system herein includes a microcalorimeter x-ray detector that depends on thermal rather than electronic x-ray detection. The microcalorimeter x-ray detector includes an absorber of individual x-ray photons that is coupled to a constant temperature thermal reservoir. The absorption of an individual photon results in a temporary spike in temperature of the absorber, which then returns to thermal equilibrium with the reservoir. In view of the small amount of energy from the absorption of a single x-ray photon, the thermal absorber has a low heat capacity at a very low temperature. Resulting temperature pulses of the absorber are measured with a thermometer that is sensitive at low temperatures.

The thermometer can be a transition-edge sensor (TES). The TES can include a thin superconducting metal film at a superconducting-normal phase transition temperature. The relatively large change in electrical resistivity of the phase transition that occurs when the film changes temperature by a small amount provides high sensitivity to the thermometer at the absorber temperature. Noise statistics of the microcalorimeter x-ray detector operated at very low temperatures are substantially lower than for conventional charge-based energy-dispersive detectors. As a result, the resolution of the microcalorimeter x-ray detectors is in the range of 1-10 eV instead of 120 electron volts. Because the energy range is provided by physical dimensions and characteristics of the absorber, the energy resolution of the microcalorimeter x-ray detector, delta E, is about 1/2000 of a total energy range of the microcalorimeter x-ray detector. The microcalorimeter x-ray detector provides a vast improvement in energy resolution over conventional charge-based detectors while covering the same energy range.

Advantageously and unexpectedly, the x-ray spectrometer system acquires pulses from thermal detectors, processes the pulses with high energy resolution, and adds pulses into an energy histogram in real time. Beneficially, the x-ray spectrometer system provides real time analysis of data collected from thermal detectors for x-ray spectroscopy. The x-ray spectrometer system also provides analysis of pulses produced by the thermal detectors according to energies with a high energy resolution. The x-ray spectrometer system further provides maximum count rates from a multiple input analyzer. Additionally, the x-ray spectrometer system determines an underlying pulse shape of each thermal detector.

The thermal spike produced by a thermal detector has a characteristic rise time determined by the geometry, mass, and specific heat of the thermal detector. The thermal detectors individually have a characteristic relaxation time determined by connection to a low temperature reservoir, and the thermal detectors have a unique output pulse shape in response to adsorption of a photon of fixed energy. The pulse shape can change as a function of the energy absorbed. The pulse shape can be used to reject distorted pulses, to remove pulse broadening, and to construct a filter that passes selected pulses and rejects noise.

Moreover, the x-ray spectrometer system provides a linear output so that measured pulse heights can be related to incident photon energies. Electronics used to amplify current pulses from the thermal detectors include superconducting quantum interference devices (SQUIDs), a SQUID as a first stage amplifier that converts the current pulse from the thermal detector to a Josephson voltage, and a SQUID array to amplify voltage for room temperature analog electronics. SQUIDs have ultralow impedance and low noise characteristics, but SQUIDs are nonlinear over large excursions. Nonlinearity of SQUIDs can lead to a nonlinear response for pulses of large amplitude, and SQUIDs can have points of stability referred to as flux quanta and a signal that transitions from one point of stability to another, referred to as flux jump.

Further, the x-ray spectrometer system rejects pulses that are distorted by overlapping multiple pulses (referred to as pulse pile up), flux jumps, and the like. By acquiring pulses that are a linear multiple of underlying pulse shape, the x-ray spectrometer system determines an x-ray spectrum of a sample.

The x-ray spectrometer system also provides spectra on a calibrated scale by collecting spectra from a known sample that emits x-rays in multiple characteristic transitions at discrete energies. From this data, a nonlinear calibration function for each thermal detector is made. The output of the x-ray spectrometer system is then made linear with energy for the thermal detectors.

Also, the x-ray spectrometer system collects data simultaneously from the thermal detectors. The x-ray spectrometer system sums outputs of the thermal detectors on an energy scale so that the count rate of the x-ray spectrometer system is greater than for one thermal detector.

It is contemplated that the x-ray spectrometer system can include a cryostat housing thermal detectors and SQUID amplifiers, electronics to condition signals and perform analogue to digital and digital to analogue conversions, and a computing system to control the system and collect data. The x-ray spectrometer system can be aligned with a source of x-radiation and can collect and analyze x-ray spectra. Excitation sources can include, e.g., an electron microscope with an electron beam for irradiating a sample, a synchrotron with an x-ray beam, and the like.

In an embodiment, with reference to FIG. 1, x-ray spectrometer system 110 includes excitation source 112 that produces excitation particles 114 and irradiates sample 116 with excitation particles 114 such that sample 116 produces x-rays 118 in response to irradiation with excitation particles 114; a plurality of thermal detectors 122 that includes a micro-calorimeter absorber and a transition edge sensor. Thermal detectors 122 detect x-rays 118 from sample 116 and produce digital x-ray data 130 in response to detecting x-rays 118 from sample 116. X-ray data 130 includes a plurality of x-ray pulses. X-ray spectrometer system 110 also includes analyzer 150 that includes multichannel receiver 132 that receives, in parallel, digital x-ray data 130 from thermal detectors 122. Analyzer 150 rejects pulse pileup in digital x-ray data 130 and produces pass data from digital x-ray data 130; subjects the pass data to a digital filter (e.g., a Wiener filter) to produce filter data; determines a pulse height of x-ray pulses in the filter data to produce pulse data; combines the pulse data to produce combined data; and calibrates the combined data to produce calibrated data in which analysis is performed, in real time, on the x-ray pulses from thermal detectors 122.

According to an embodiment, with reference to FIG. 1, excitation particles 114 (e.g., electrons, photons, and the like) are generated by source 112 that irradiates sample 116. Resulting atomic excitations produce characteristic x-rays 118 that are used to identify elements in sample 116.

X-rays 118 are received by thermal detectors 122. Each thermal detector 122 produces a heat pulse on absorption of single x-ray photon 118 that is converted into analog voltage pulse 124. Each thermal detector 122 is connected to individual analog to digital converter 126, with analog voltage pulse 124 subject to amplification and filtering as selected.

Analog x-ray data 124 from each analog to digital converter 126 is continuously sampled at a given frequency to produce digital data 130 registered in a parallel multichannel receiver 132. A rate of digitization is selected so that a peak height of each pulse is measured to a desired accuracy.

Figure 2:
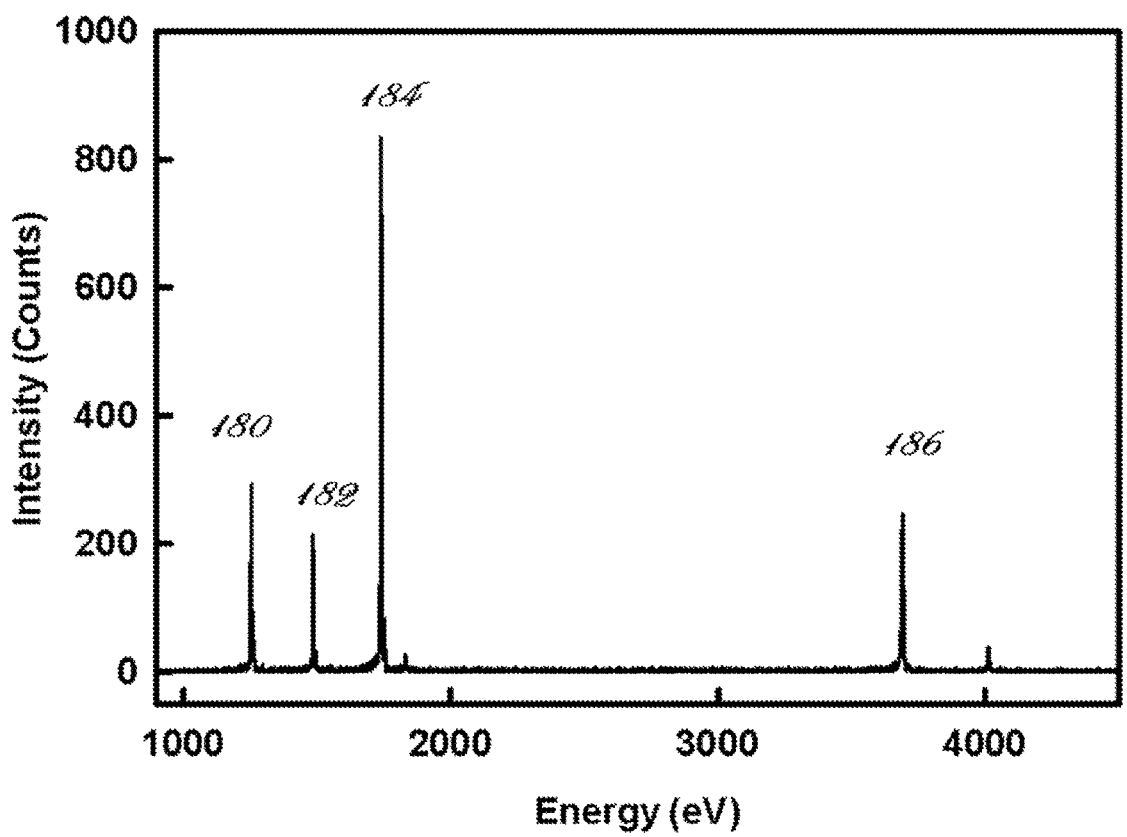
FIG. 2 shows a graph of intensity versus energy.
Figure 3:
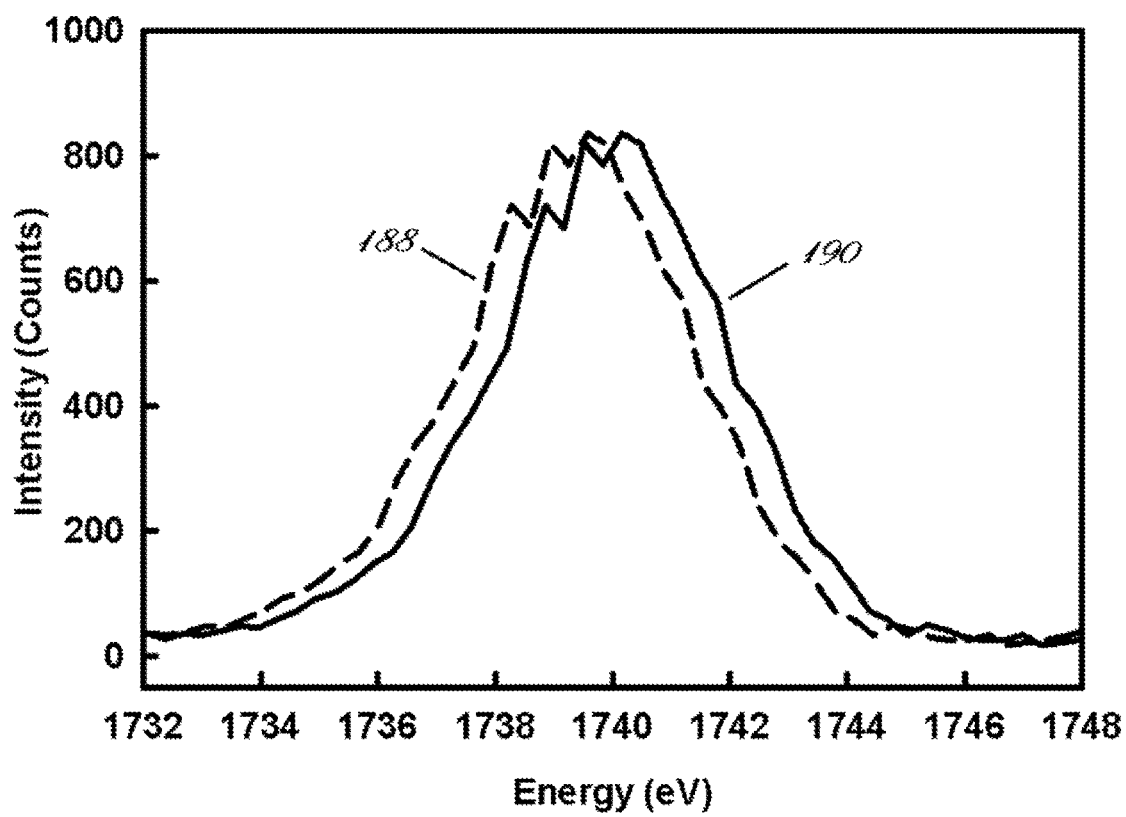
FIG. 3 shows a graph of intensity versus energy.

Analog to digital converter 126 and digital x-ray data 130 provide data to processor 134 through parallel bus 138. As pulses are processed, pulses are converted into combined data 140 to form high-resolution x-ray energy spectrum 136. An exemplary high-resolution x-ray energy spectrum 136 is shown in FIG. 2. A high-resolution energy spectrum that has shifted as a result of a chemical process is shown in FIG. 3.

Analyzer 150 receives digital x-ray data 130 from each channel of thermal detectors 122 directly to individual processing code of processor 134, wherein code for each thermal detector 122 runs independently.

Figure 4:
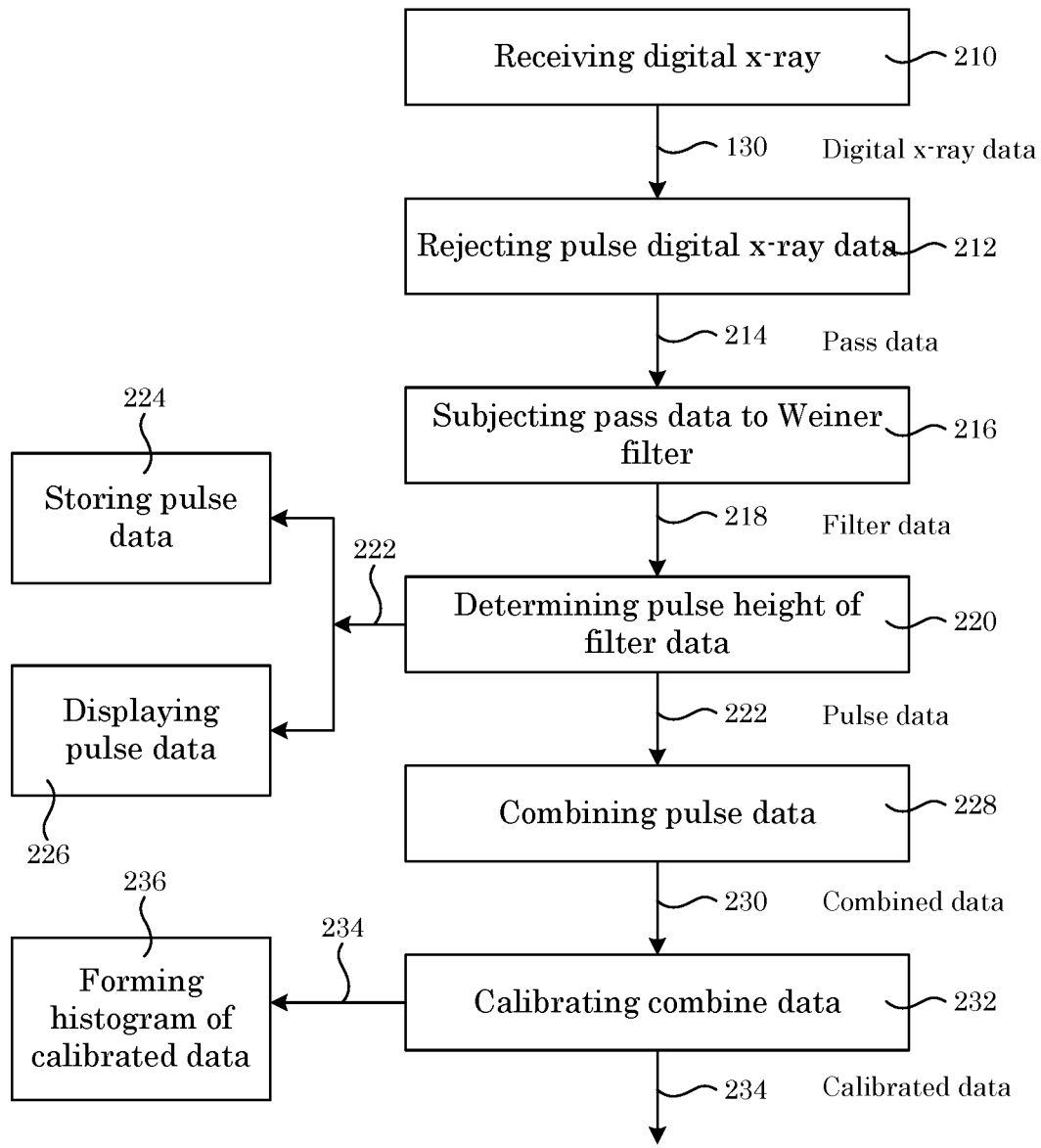
FIG. 4 shows a process for performing real time analysis of x-ray pulses.

In an embodiment, processor 134 is data flow computer in which data is processed as data becomes available (e.g., digital x-ray data 130, pass data 214, filter data 218, pulse data 222, combined data 230, calibrated data 234, and the like). In this way, each detector 122 has its data processed independently of all other thermal detectors 122. Each channel of processor 134 can run independently and in parallel with all others as shown in FIG. 4. Here, to achieve accuracy of x-ray spectrometer system 110, peak heights can be determined to an accuracy of 1 part in 2000. As shown in FIG. 4, digital x-ray data 130 (that digitally sampled) (step 210) are received by processor 134, and processor 134 rejects pulses distorted by pileup (step 212) to produce pass data 214 as remaining pulse data that is communicated to a digital filter to minimize noise from x-ray spectrometer system 110 and to produce filter data 218 (step 216). Pulse heights of filter data 218 are determined to produce pulse data 222 (step 220). Pulse data 222 can be stored (step 224) or displayed as a histogram (step 226) according to pulse height in volts. In a case of multiple thermal detectors 122 and data strings, pulse height voltage of pulse data 222 is converted to an energy and combined to produce combined data 230 (step 228). Combined data 230 can be calibrated to produce calibrated data 234, which can be stored or formed into a histogram (step 236).

In an embodiment, a process for performing real time analysis of x-ray pulses from thermal detectors 122 includes: receiving digital x-ray data 130 from thermal detectors 122 including a micro-calorimeter absorber and a transition edge sensor, digital x-ray data 130 including a plurality of x-ray pulses; rejecting pulse pileup in digital x-ray data 130 to produce pass data 214 from digital x-ray data 130; subjecting pass data 214 to a digital filter including a Wiener filter to produce filter data 218; determining a pulse height of x-ray pulses in filter data 218 to produce pulse data 222; combining pulse data 222 to produce combined data 230; and calibrating combined data 230 to produce calibrated data 234 to perform analysis, in real time, of the x-ray pulses from thermal detectors 122.

According to an embodiment, a process for performing real time analysis of x-ray pulses from a plurality of thermal detectors 122 includes: introducing sample 116 to x-ray spectrometer system 110 including thermal detectors 122, thermal detectors 122 including a micro-calorimeter absorber and a transition edge sensor; irradiating sample 116 with excitation particles 114; producing x-rays 118 by sample 116 in response to irradiation with excitation particles 114; detecting x-rays 118 by thermal detectors 122; producing digital x-ray data 130 by thermal detectors 122 in response to detecting x-rays 118 from sample 116; receiving, in parallel by multichannel receiver 132, digital x-ray data 130 from thermal detectors 122, digital x-ray data 130 including a plurality of x-ray pulses; rejecting pulse pileup in digital x-ray data 130 to produce pass data 214 from digital x-ray data 130; subjecting pass data 214 to a Wiener filter to produce filter data 218; determining a pulse height of x-ray pulses in filter data 218 to produce pulse data 222; combining pulse data 222 to produce combined data 230; and calibrating combined data 230 to produce calibrated data 234 to perform analysis, in real time, of the x-ray pulses from thermal detectors 122.

In the process for performing real time analysis of x-ray pulses from a plurality of thermal detectors 122, introducing sample 116 to x-ray spectrometer system 110 includes positioning a sample to be irradiated by the excitation radiation and to emit radiation in the direction of the spectrometer.

In the process for performing real time analysis of x-ray pulses from a plurality of thermal detectors 122, irradiating sample 116 with excitation particles 114 includes creating a source of the exciting particles positioned such that the sample is exposed to said particles.

In the process for performing real time analysis of x-ray pulses from a plurality of thermal detectors 122, producing x-rays 118 by sample 116 in response to irradiation with excitation particles 114 includes further aligning the sample so that characteristic radiation from the sample constituents can readily escape the sample and strike the detectors.

In the process for performing real time analysis of x-ray pulses from a plurality of thermal detectors 122, detecting x-rays 118 by thermal detectors 122 includes continuous analog measurement of individual detector temperatures with a thermometer with a rapid electrical response so as to generate an electrical pulse when an x-ray is absorbed on a detector with resulting heat.

In the process for performing real time analysis of x-ray pulses from a plurality of thermal detectors 122, producing digital x-ray data 130 by thermal detectors 122 in response to detecting x-rays 118 from sample 116 includes continuous analog to digital conversion of electrical pulses by means of digital sampling and testing of samples for initiation of a pulse; storage of the pulse samples and samples of pre-pulse baseline.

In the process for performing real time analysis of x-ray pulses from a plurality of thermal detectors 122, receiving, in parallel by multichannel receiver 132, digital x-ray data 130 from thermal detectors 122, digital x-ray data 130 including a plurality of x-ray pulses includes sending pulses from all detectors over a parallel bus line to a computer processor to process pulses using separate cores in parallel In the process for performing real time analysis of x-ray pulses from a plurality of thermal detectors 122, subjecting pass data 214 to a Wiener filter to produce filter data 218 includes creating a Wiener filter from an average of pulses and a spectrum of system noise in each channel, then filtering incoming data to minimize pulse noise.

In the process for performing real time analysis of x-ray pulses from a plurality of thermal detectors 122, determining a pulse height of x-ray pulses in filter data 218 to produce pulse data 222 includes a least-squares fitting of a polynomial function to the maximum of the peak to determine pulse height and the subsequent calculation of pulse area In the process for performing real time analysis of x-ray pulses from a plurality of thermal detectors 122, rejecting pulse pileup in digital x-ray data 130 to produce pass data 214 from digital x-ray data 130 includes comparison of pulse height versus pulse area and rejecting pulses with a less than the selected correlation.

In the process for performing real time analysis of x-ray pulses from a plurality of thermal detectors 122, combining pulse data 222 to produce combined data 230 includes calibrating the energy range of spectra from individual detectors using a standard sample and applying the calibrations to allow combining results from individual detectors.

In the process for performing real time analysis of x-ray pulses from a plurality of thermal detectors 122, calibrating combined data 230 to produce calibrated data 234 includes producing a histogram of pulses calibrated to a common energy scale and storing it.

Excitation source 112 dynamically controls access to excitation particles 114 and can include various components. Excitation source 112 can be a device that emits photons or charged particles or a radioactive source that emits photons or charged particles and can be part of a system that emits and accelerates charged particles.

In x-ray spectrometer system 110, excitation particles 114 can include x-rays, gamma rays, electrons, or other charged particles to ionize atoms in a sample material and can be atoms that are within the penetration depth of the excitation particles. Moreover, the photons or charged particles must be of an energy that causes atoms to transition into states of energy of more than 100 electron volts above their ground state.

In x-ray spectrometer system 110, sample 116 can include matter whose atoms or nuclei can be excited by an excitation source or by its own radioactive decay and which gives off x-rays or gamma rays as a result and can be a solid, liquid, or gas. Moreover, the sample can be disposed in a presence of the detector.

In x-ray spectrometer system 110, x-rays 118 can include photons resulting from the decay of an excited atomic or nuclear state and can be of an energy to produce a measurable temperature rise in a thermal absorber. Moreover, the photons can be of any polarization.

In x-ray spectrometer system 110, thermal detectors 122 can include thermal absorbers and can be elements that have a low specific heat at low temperatures. Moreover, the absorbers can be in a semi-metallic, semiconducting, or superconducting state.

In x-ray spectrometer system 110, analog voltage pulse 124 can include the result of a temperature measurement on the absorber that has just absorbed an x-ray photon such that the temperature measurement resulting in the absorber in a rise of temperature when a photon is absorbed and a subsequent decay as the absorber cools down and can be the result of the resistance change of a superconducting film going normal at its transition, or the resistance change of a semiconductor that goes more conducting during a temperature rise. Moreover, the analog pulse can be the result of an electronic amplification of such a resistance change or of a feedback circuit that maintains the thermometer at a constant bias or value.

In x-ray spectrometer system 110, analog to digital converter 126 can include an electronic device that converts a continuously varying signal voltage to a series of numerical readings for digital calculation in the analysis of said signal and can sample the signal voltage and produce readings at a selected rate. Moreover, the readings can be over a range of fixed levels of constant spacing determined by the division of a binary number.

In x-ray spectrometer system 110, digital x-ray data 130 can include a time series of digital samples to determine a baseline level before the detection of an x-ray photon, the point at which the pulse corresponding to the detection of the x-ray photon crosses a threshold, the point at which a maximum of the response to the x-ray photon occurs, and the subsequent decay of the response back to the baseline and can be the result of a current or voltage analog pulse that is converted into a series of digital data by means of an analog to digital converter. Moreover, digital x-ray data may be produced in real time, or stored in advance and read at a later time.

In x-ray spectrometer system 110, multichannel receiver 132 can include a plurality of analogue to digital converters that gather data at a rate sufficient to ensure the thermal pulse properties can be subsequently deduced from the digital data from each of the plurality of temperature detectors and can be arranged on suitable high speed buses to ensure the computing system is able to analyze the data in real time. Moreover, the analogue to digital data conversion system must provide sufficient speed to ensure the signal is captured with full fidelity for all of a plurality of detectors.

In x-ray spectrometer system 110, processor 134 can include a central processor unit with sufficient speed so that data from the plurality of detectors is processed according to processes herein and can be a data flow computing system where the data from each detector arrives at a processor asynchronously and is processed immediately. Such a processor can be disposed within a single computer or can be distributed in several computers. Moreover, the implementation of such a data flow computing system may be structured around a software computing language that executes processes herein a computer.

In x-ray spectrometer system 110, high-resolution x-ray energy spectrum 136 can include a histogram in which counts of pulses are sorted according to their amplitudes which have been converted for each detector into energies of the initial photons to provide a record of the frequency of photon energies emitted by the sample and can be calibrated by comparison of pulse amplitudes of x-rays emitted by a sample with known energies. Moreover, the energy calibration can be accomplished by taking a histogram of a sample designated as a standard for its energies. The resolution of the x-ray energy spectrum is determined by the initial resolution of the A/D converter and the level of noise in the system.

In x-ray spectrometer system 110, parallel bus 138 can include the input/output bus of a computing system to deliver the data created through the analog to digital conversion process to the central processing unit or units and can belong a computer.

In x-ray spectrometer system 110, combined data 140 can include pulse heights reported by processing pulses from multiple detectors and calibration information from each detector to create a histogram of pulse heights and can include pulse heights that are corrected with respect to the individual properties of each detector. Moreover, the correction can be expressed in terms of a pulse energy corresponding to the pulse height so that the histogram is a spectrum calibrated in energy.

In x-ray spectrometer system 110, analyzer 150 can include a computing system with software to measure the height of each pulse from all detectors and can be a dataflow computing system with parallel connections to analogue-to-digital convertors connected to the plurality of temperature detectors. Moreover, system of computation has a speed and parallel architecture such that all pulses are measured to produce output in real time.

In x-ray spectrometer system 110, pass data 214 can include digital samples of pulses that have been subjected to quantitative criteria to determine that the pulses do not contain overlaps of additional pulses and can be used to create a histogram of pulse heights. Moreover, the histogram of pulse heights without contamination by overlaps will represent a true spectrum of pulse energies and pulse widths once calibrated to convert pulse height to energy.

In x-ray spectrometer system 110, filter data 218 can include digital samples of pulses that have been subjected to digital filtering to remove noise in the pulse amplitudes and can be the pulses that give the least error in amplitude owing to the presence of noise (e.g., a Wiener filter). Moreover, filter data originating from a single x-ray line will give the least variation in pulse height, or correspondingly, in energy, once calibrated.

In x-ray spectrometer system 110, pulse data 222 can include the digitized values of pulse heights determined by a polynomial fit to the peak of pulses specified by digitally sampled pulse data to provide a histogram of pulse heights and can be values determined from pulses that have already been selected successfully for the absence of overlapping pulses. Moreover, pulse data can be calibrated for energy when a conversion factor has been established from measurements of a standard sample.

In x-ray spectrometer system 110, combined data 230 can include pulse data that has been converted from pulse amplitudes to pulse energies using a conversion function that varies to compensate for differences in the performance of individual detectors and can be combined from several detectors for output in a histogram. Moreover, combined data has uniform relationship between the distribution of x-ray energies detected and the values of energy contained in the combined data independent of the detector from which it originates.

Figure 5:
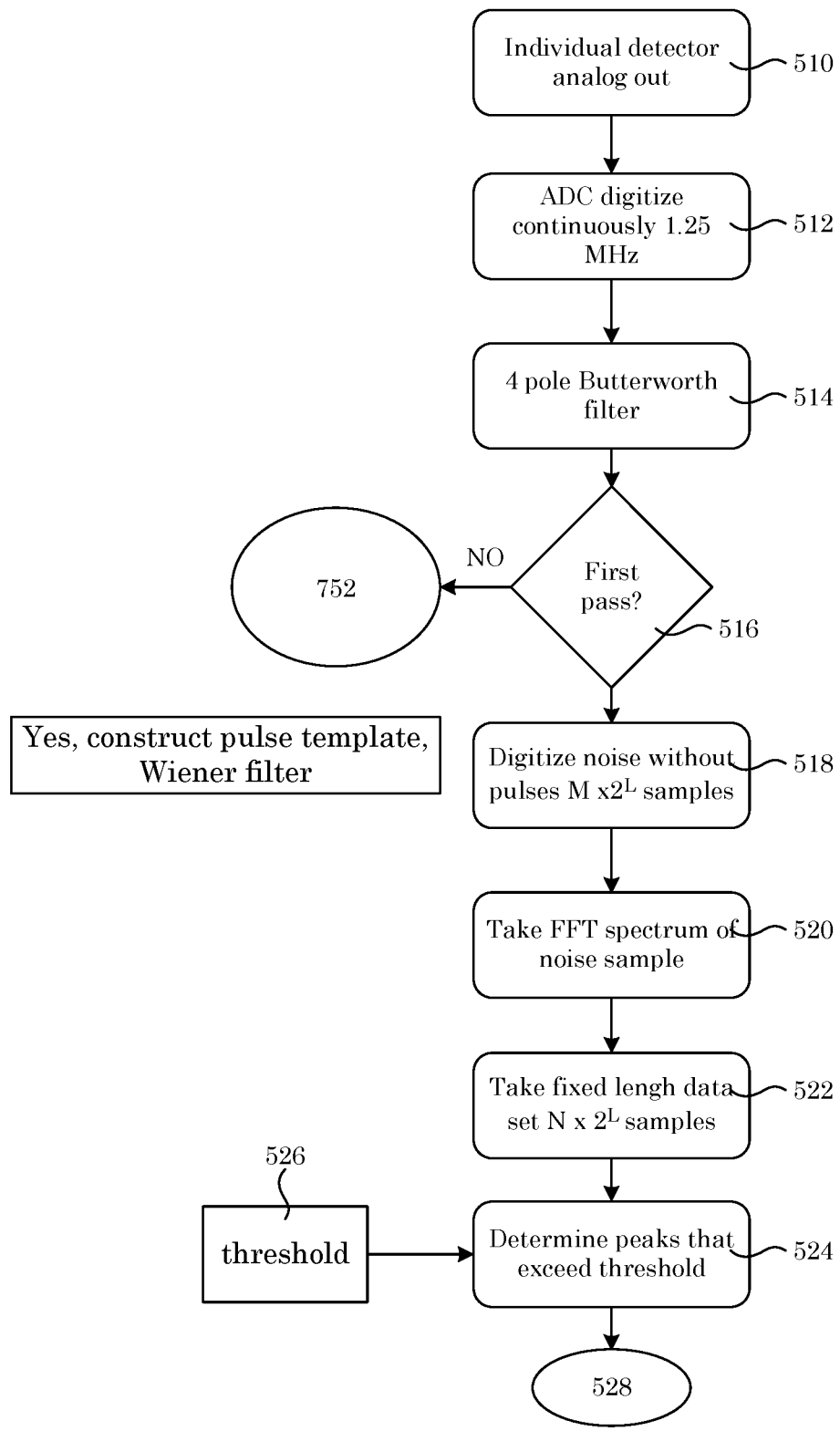
FIG. 5 shows a process for performing real time analysis of x-ray pulses.

In x-ray spectrometer system 110, calibrated data 234 can include pulse data that has been converted from pulse amplitudes to pulse energies using a conversion function to relate the assigned energy to pulse energies obtained from calibrated standard x-ray lines and can be amplitudes of any value which do not exceed the amplitudes limited by the calibrated x-ray lines. Moreover, the calibrated data may originate from pulse amplitudes of any values lying between the amplitudes of pulses from the calibrated x-ray lines Details of the process for performing real time analysis of x-ray pulses from a plurality of thermal detectors 122 are shown FIG. 5, FIG. 6, FIG. 7, FIG. 8, FIG. 9, FIG. 10, FIG. 11, and FIG. 12. Here, the following description pertains to each channel of thermal detectors 122. As shown in FIG. 5, starting with analog voltage pulse 124 from any of thermal detectors 122 (step 510), analog voltage pulse 124 is sampled continuously at a selected rate (e.g., 1.25 MHz) by analog to digital converter 126 (step 512). The sampled signal is passed through a digital 4-pole Butterworth filter (step 514) to reduce noise above a certain passband. At the beginning of acquiring a spectrum, i.e., for a first pass in which a new spectrum is to be acquired, a pulse template and noise spectrum (exemplary elements for construction of an optimal digital filter (e.g., Wiener filter)), are initiated (step 516); otherwise, for continuing data analysis, the process continues at step 752 with application of a Wiener filter. For the beginning of acquiring the spectrum, a noise spectrum without pulses is sampled by each analog to digital converter 126 in which the noise spectrum includes M blocks, and each block include a binary number of samples (i.e., $2^L$ samples) (step 518).

Figure 6:
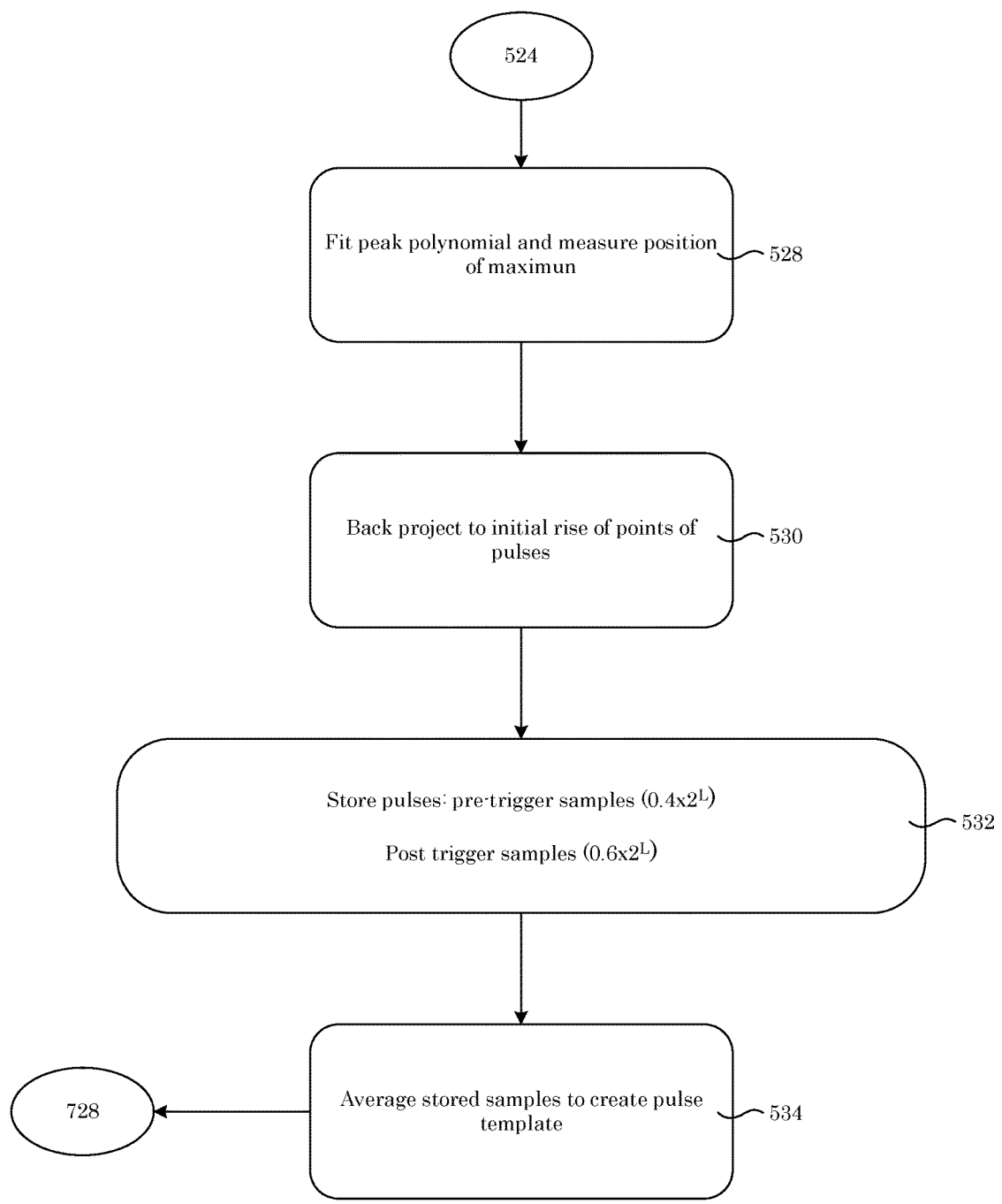
FIG. 6 shows a continuation of the process for performing real time analysis of x-ray pulses of FIG. 5.

The noise sample is subjected to a fast Fourier transform (FFT) to convert the noise sample into a spectrum (step 520). A model pulse is used to create a Wiener filter. Here, a data block is recorded with pulses that include N pulses, wherein each data block includes a binary number of $2^L$ samples (step 522). Pulses that exceed a selected threshold (step 526) are identified (step 524) and passed to step 528 shown in FIG. 6, wherein peak position for each pulse is determined by fitting the pulse to a polynomial (step 528). A rise time of the pulse is used to identify a sample number that includes a starting point or trigger point of the pulse (step 530). Here, back projection provides the initial rise point. A fraction of pre-trigger samples, e.g., 40%, and a fraction of post-trigger samples, e.g., 60% of the post-trigger samples are stored for each pulse (step 532). Step 522 to step 532 shown in FIG. 5 and FIG. 6 are aggregately referred to as "Take fixed length data set" (step 800) in FIG. 10.

Figure 7:
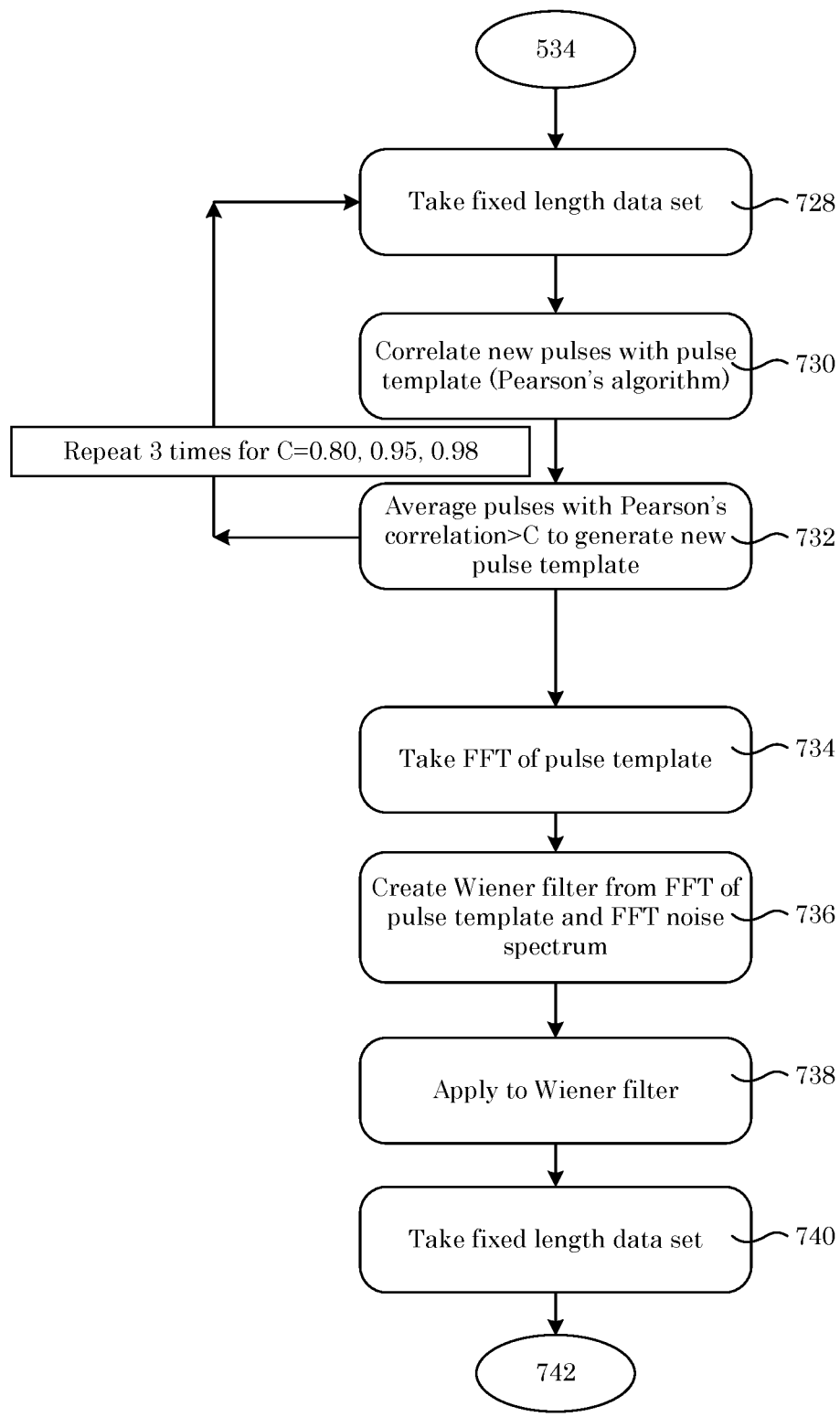
FIG. 7 shows a continuation of the process for performing real time analysis of x-ray pulses of FIG. 6.

The digitized samples of stored pulses are averaged to create the pulse template (step 534). With reference to FIG. 7, a new fixed length data set is obtained in step 728 by subjecting new additional digitized pulse samples to step 800 that repeats step 522 to step 532 on the new additional pulse samples. The stored pulses of the new set fixed length data set are compared to the first template using Pearson's correlation function (step 730). Pulses with a correlation coefficient greater than a selected value of C, e.g., C=0.80, are retained (step 732), wherein C is an arbitrarily selected value Pearson's coefficient. These pulses are averaged to create a new template for which step 728 to step 732 is repeated for further selected values of C, e.g., selected values of C that could be 0.95 and 0.98 until the pulse shows no sign of change. The resulting average pulse is retained as the template as the input to step 734 in which a Fourier transform of the pulse template is obtained by performing an FFT (step 734).

A Wiener filter is created from a noise power spectrum and the pulse template FFT (step 736). The Wiener filter is applied to further data sets (step 738), and a new data set is obtained therefrom (step 740) by applying take fixed length data set (800 shown in FIG. 10).

Figure 8:
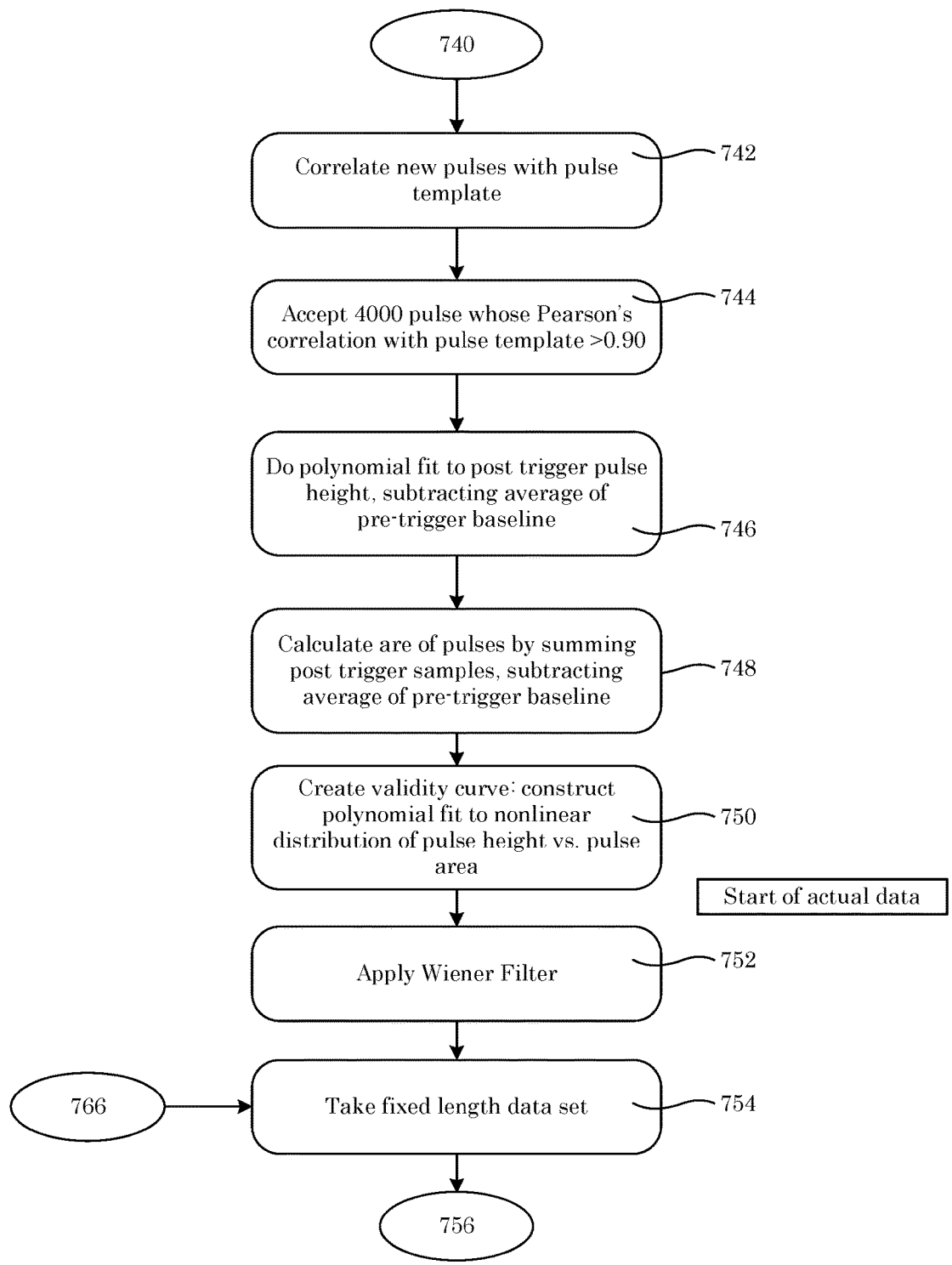
FIG. 8 shows a continuation of the process for performing real time analysis of x-ray pulses of FIG. 7.

Pulses are correlated with the pulse template using Pearson's correlation function (step 742) as shown in FIG. 8. A selected number of pulses (e.g., 4000 pulses) with a correlation coefficient that can be greater than 0.90 are recorded (step 744). Pulse heights are obtained from a polynomial fit to each peak height minus a mean value of a baseline of each successful pulse (step 746). An area of each successful pulse is obtained by summing post-trigger samples and subtracting an average of a pre-trigger sample baseline (step 748).

Figure 10:
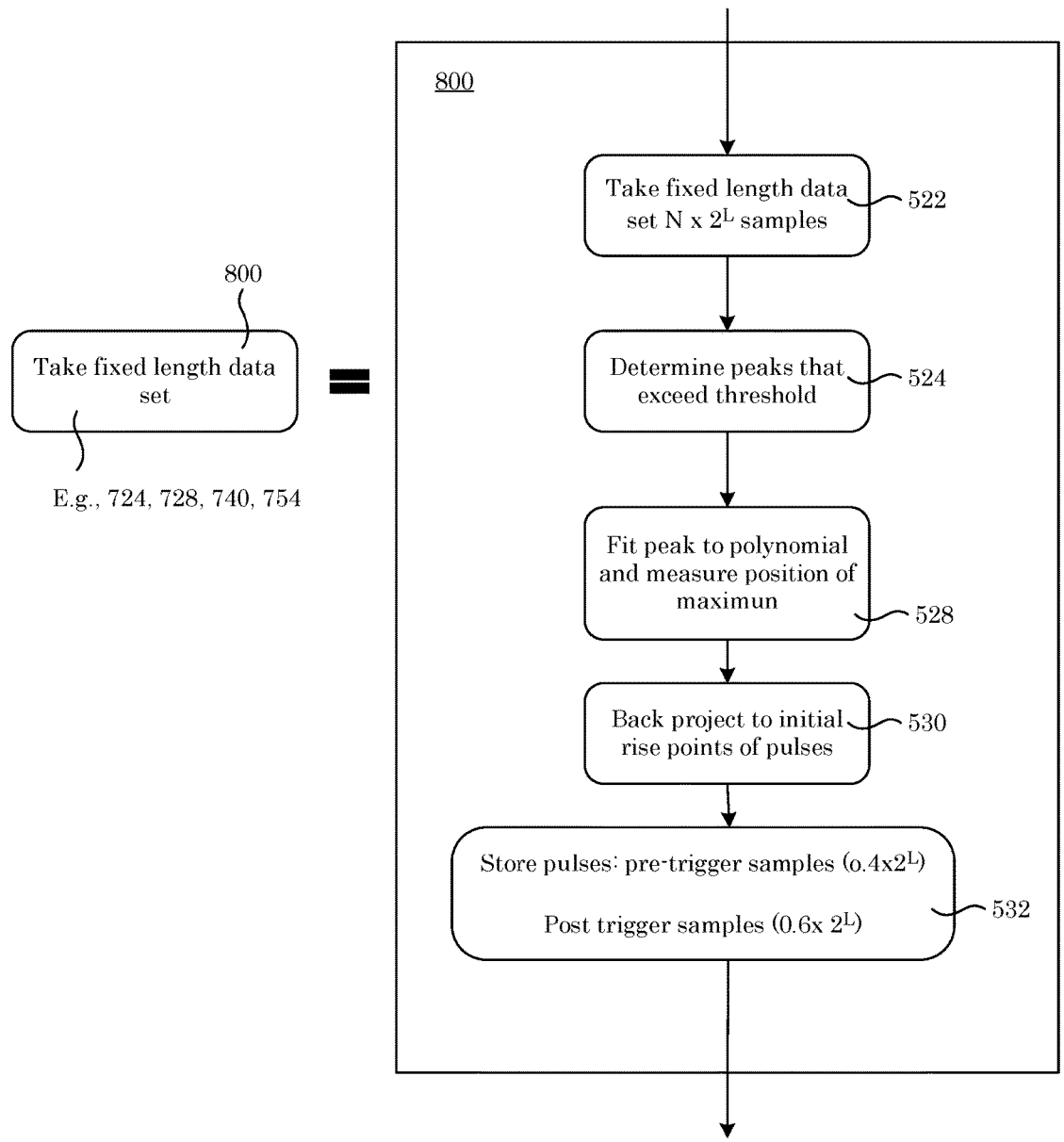
FIG. 10 shows a process for taking a fixed length data set.

A nonlinear validity curve is made by fitting a table of pulse heights of the, e.g., 4000, successful pulses versus areas of the pulses with a polynomial (step 750). Because of differing physical properties, an individual validity curve is constructed for individual thermal detectors 122. Pulses that pass the validity curve are used to construct the histogram of pulse heights (in volts) or a histogram of energies if a calibration file is available. At this point (step 752), the actual data for a spectrum are recorded for new additional pulse samples obtained by activating the Wiener filter (step 752) and taking a fixed length data set (step 754) as shown in FIG. 10 (800).

Figure 9:
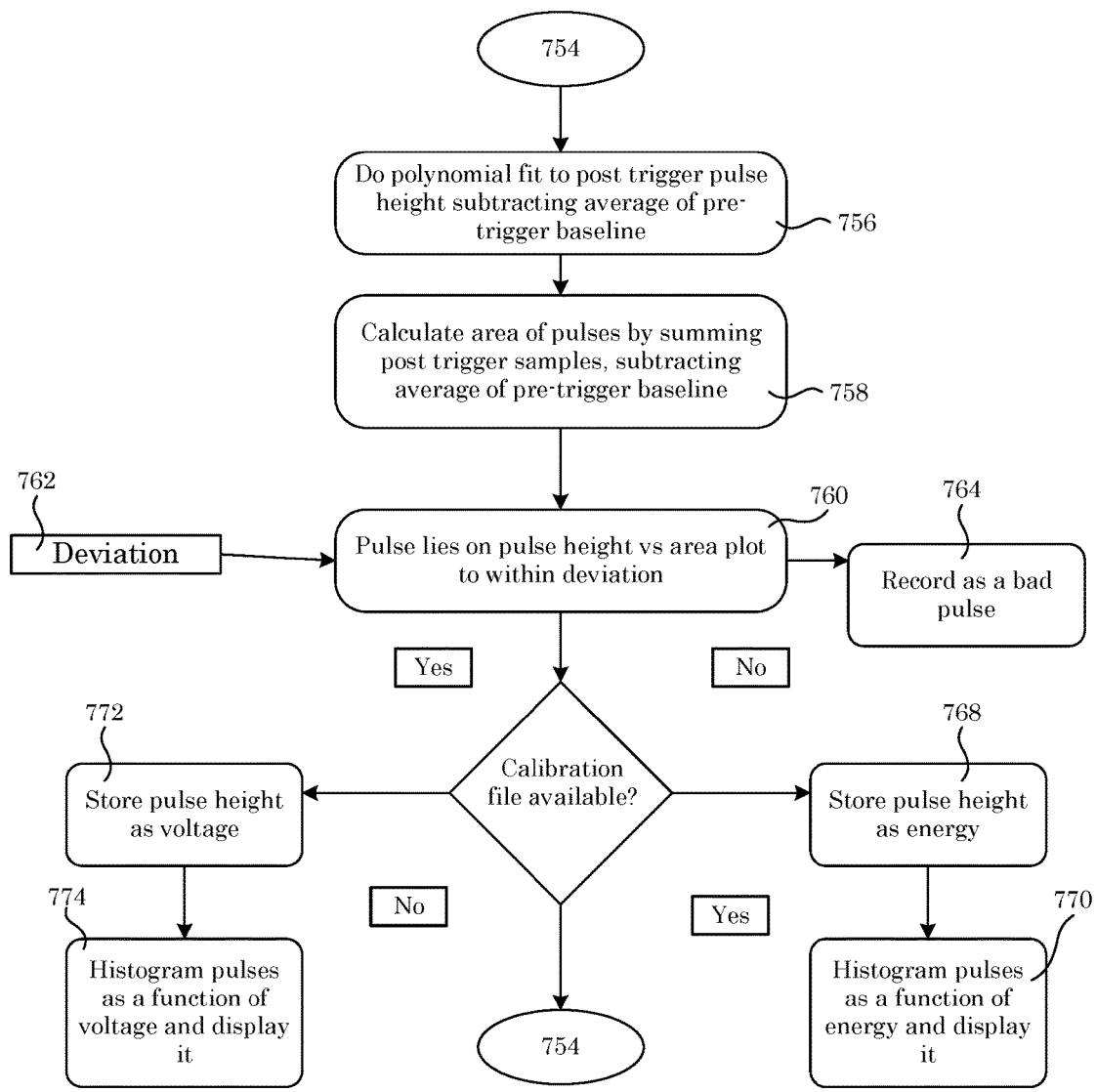
FIG. 9 shows a continuation of the process for performing real time analysis of x-ray pulses of FIG. 8.

With reference to FIG. 9, pulse heights are obtained by fitting the post trigger pulse height to a polynomial after subtracting the average of the pre-trigger baseline (step 756) from the data set produced in step 754. Areas of the pulses are determined by summing post-trigger samples after subtracting the average of the pre-trigger baseline (step 758). If the pulse lies on the pulse height versus pulse area plot to within a selected deviation (step 762), the pulse height is included in a histogram (step 760); otherwise, the pulse is recorded as a bad pulse (step 764) and not included in the histogram.

If a calibration file is already available (step 766), the pulse height is converted to an energy, and recorded (step 768), and displayed in a histogram of energy (step 770). Otherwise, the pulse height is recorded (step 772) and displayed in a histogram of pulse height voltage (step 744). A spectrum of arbitrary length can be obtained by repeating step 754 to step 766.

Figure 11:
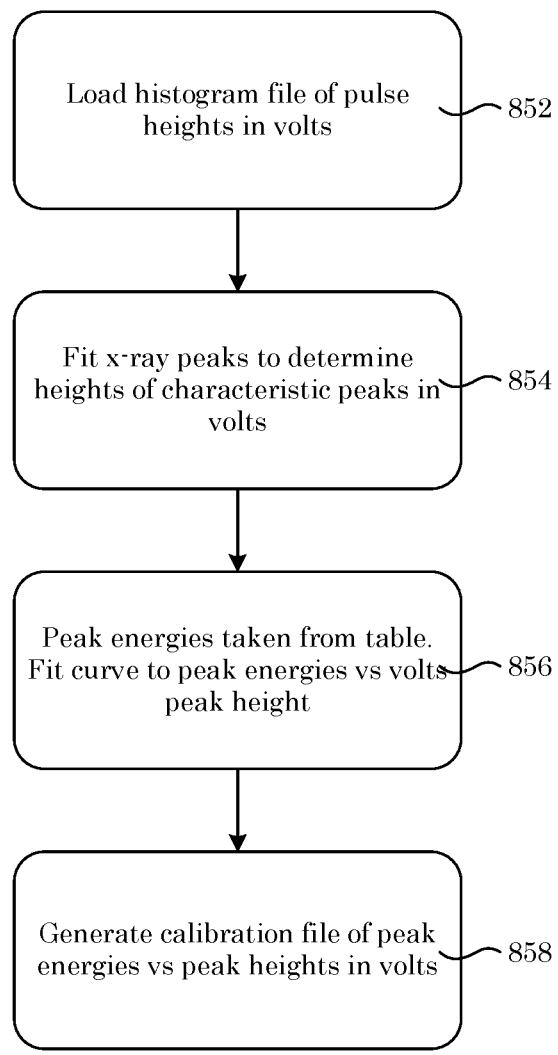
FIG. 11 shows energy calibration.

It is contemplated that thermal detectors 122 may not have an absolute calibration. In an embodiment, thermal detectors 122 are calibrated by comparing x-ray peak positions in a histogram of pulse energies against a table of energies of known element lines as shown in FIG. 11. Here, x-ray spectrum is obtained from analog voltage pulse 124 output by thermal detectors 122 from a standard calibration sample, wherein peaks in a histogram of pulse heights in volts (step 852) are fitted to obtain peak locations (step 854) in volts. Peak locations of known elements in volts are fitted to a table of corresponding peak energies of the same elements (step 856) to obtain a calibration function. Within a given range of pulse heights in volts from a given detector, the calibration function converts pulse heights into pulse energies for pulses of any height. This is accomplished by storing the parameters of the calibration function in a file from which it can be recreated. (step 858).

Figure 12:
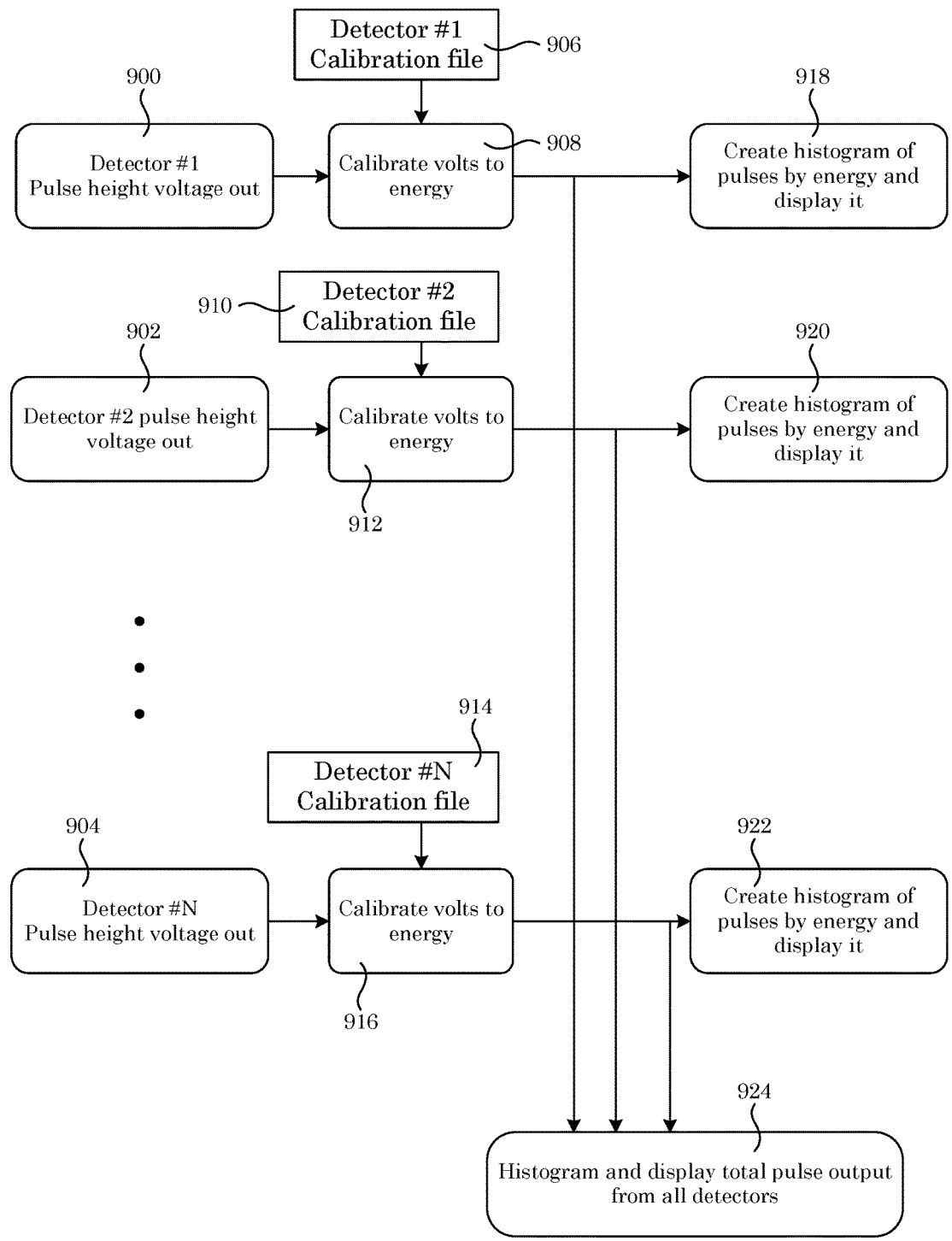
FIG. 12 shows combining data from a plurality of thermal detectors.

Combined spectra from all thermal detectors 122 are obtained as shown in FIG. 12, wherein each thermal detectors 122 has an individual calibration file (steps 906, 910, 914, and the like). When calibration files are acquired, pulses from individual thermal detectors 122 (steps 900, 902, 904, and the like) are calibrated to a same energy scale (steps 908, 912, 916, and the like). Individual histograms of pulses sorted by energy are recorded (steps 918, 920, 922, and the like). Results are collected as a collective histogram and displayed (step 924).

X-ray spectrometer system 110 and processes herein have numerous advantageous and beneficial properties that include detection of individual x-ray photons; determination of energy of individual x-ray photons over a wide range of energies; determination of the energy of the x-ray photons to greater resolution than conventional energy dispersive detectors; determination of energy of the x-ray photons to greater precision than conventional energy dispersive detectors; determination of idealized pulse shape from each detector; implementation of resolution and precision by real time identification and rejection of superimposed pulses (pulse pileup) using correlation with an idealized pulse; implementation of resolution and precision by real time identification and rejection of superimposed pulses (pulse pileup) using a function that correlates pulse height and area; implementation of resolution and precision by real time calibration with respect to elemental standard lines; creation of an optimal digital filter from noise and the idealized pulse shape for each detector; implementation of resolution and precision by real time optimal digital filtering of digitized pulses; implementation of resolution and precision by fitting of polynomial function to peak height; implementation of combining spectra from separate detectors with resolution and precision by means of individual real time calibrations with respect to elemental standard lines; acquisition of energy-calibrated spectra from an individual detector in real time as a histogram; determination of energy-calibrated spectra summing over multiple detectors in real time as a histogram; production of optimal digital filter from noise and live spectra of the system; production of energy calibration from live spectra of the system with a standard sample; receipt of pulses from multiple detectors; organization of pulses from multiple detectors for real time parallel processing; receipt and process of digital pulses continuously in parallel from multiple detectors; implementation of dataflow to process pulses from multiple detectors continuously in different parts of the system; expansion of the number of detectors with increased parallel processing; and the like.

Embodiments of the subject matter and the operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions, encoded on a computer storage medium for execution by, or to control the operation of, data processing apparatus. Alternatively, or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more computers executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, workstations, or any other kind of central processing unit. Generally, a central processing unit will receive instructions and data from a read-only memory or a random-access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic; magneto-optical disks, optical disks, USB drives, and so on. However, a computer need not have such devices. Moreover, a computer can be embedded in another device, e.g., a mobile telephone, a personal digital assistant (PDA), a microwave oven, mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The central processing unit and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks). Such interconnects may involve electrical cabling, fiber optics, or be wireless connections.

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A process for performing real time analysis of x-ray pulses from a plurality of thermal detectors, the process comprising:
    introducing a sample to an x-ray spectrometer comprising the thermal detectors, the thermal detectors comprising a micro-calorimeter absorber and a transition edge sensor;
    irradiating the sample with excitation particles;
    producing x-rays by the sample in response to irradiation with the excitation particles;
    detecting the x-rays by the thermal detectors;
    producing digital x-ray data by the thermal detectors in response to detecting the x-rays from the sample;
    receiving, in parallel by a multichannel receiver, the digital x-ray data from the thermal detectors, the x-ray data comprising a plurality of x-ray pulses;
    rejecting pulse pileup in the digital x-ray data to produce pass data from the digital x-ray data;
    subjecting the pass data to a Wiener filter to produce filter data;
    determining a pulse height of x-ray pulses in the filter data to produce pulse data;
    combining the pulse data to produce combined data; and
    calibrating the combined data to produce calibrated data to perform analysis, in real time, of the x-ray pulses from the thermal detectors.

2. A process for performing real time analysis of x-ray pulses from a plurality of thermal detectors, the process comprising:
    receiving digital x-ray data from the thermal detectors comprising a micro-calorimeter absorber and a transition edge sensor, the x-ray data comprising a plurality of x-ray pulses;
    rejecting pulse pileup in the digital x-ray data to produce pass data from the digital x-ray data;
    subjecting the pass data to a Wiener filter to produce filter data;
    determining a pulse height of x-ray pulses in the filter data to produce pulse data;
    combining the pulse data to produce combined data; and
    calibrating the combined data to produce calibrated data to perform analysis, in real time, of the x-ray pulses from the thermal detectors.

3. An x-ray spectrometer system comprising:
    an excitation source that produces excitation particles and irradiates a sample with the excitation particles such that the sample produces x-rays in response to irradiation with the excitation particles;
    a plurality of thermal detectors, the thermal detectors comprising a micro-calorimeter absorber and a transition edge sensor, and that:
        detects the x-rays from the sample; and
        produces digital x-ray data in response to detecting the x-rays from the sample, the x-ray data comprising a plurality of x-ray pulses; and
    an analyzer that comprises a multichannel receiver that receives, in parallel, the digital x-ray data from the thermal detectors and that:
        rejects pulse pileup in the digital x-ray data and produces pass data from the digital x-ray data;
        subjects the pass data to a Wiener filter to produce filter data;
        determines a pulse height of x-ray pulses in the filter data to produce pulse data;
        combines the pulse data to produce combined data; and
        calibrates the combined data to produce calibrated data in which analysis is performed, in real time, on the x-ray pulses from the thermal detectors.

* * * * *